( 12 ) United States Patent
Pracar et al.

(10) Patent No.: US 9,959,775 B2
(45) Date of Patent: May 1, 2018

(54) MONITORING, TRACKING, AND MANAGING SYMPTOMS OF ALZHEIMER'S DISEASE

(71) Applicants: Alexis Pracar, Piedmont, CA (US); Shane Pracar, Piedmont, CA (US)

(72) Inventors: Alexis Pracar, Piedmont, CA (US); Shane Pracar, Piedmont, CA (US)

( * ) Notice: Subject to any disclaimer, the term of this patent is extended or adjusted under 35 U.S.C. 154(b) by 428 days.

(21) Appl. No.: 14/021,426

(22) Filed: Sep. 9, 2013

(65) Prior Publication Data

US 2015/0072324 A1    Mar. 12, 2015

(51) Int. Cl.
    A61B 5/16    (2006.01)
    G09B 7/00    (2006.01)
    A61B 5/00    (2006.01)

(52) U.S. Cl.
    CPC .......... *G09B 7/00* (2013.01); *A61B 5/16* (2013.01); *A61B 5/4088* (2013.01); *A61B 5/742* (2013.01)

(58) Field of Classification Search
    CPC ............ A61B 5/165; G01N 2800/28; G01N 2800/2814; G01N 2800/2821
    USPC ................................. 434/236, 238
    See application file for complete search history.

(56) References Cited

U.S. PATENT DOCUMENTS

| 9,251,713 | B1* | 2/2016 | Giovanniello | G09B 5/00 |
| 2004/0034286 | A1* | 2/2004 | Kasper | A61B 5/0002 600/300 |
| 2005/0143630 | A1* | 6/2005 | Darby | A61B 5/16 600/300 |
| 2008/0057483 | A1* | 3/2008 | Avidan | G09B 21/00 434/362 |
| 2008/0058664 | A1* | 3/2008 | Mirro | A61N 1/37211 600/523 |
| 2009/0322513 | A1* | 12/2009 | Hwang | A61B 5/02055 340/539.12 |
| 2010/0217096 | A1* | 8/2010 | Nanikashvili | A61B 5/02438 600/301 |
| 2010/0250179 | A1* | 9/2010 | Mariano | A63K 3/00 702/96 |
| 2011/0236864 | A1* | 9/2011 | Ashford | A61B 5/4088 434/236 |
| 2012/0050685 | A1* | 3/2012 | Bartlett | A61B 3/0033 351/223 |

(Continued)

OTHER PUBLICATIONS

"Alzheimer's Disease", Wikipedia, [Online]. Retrieved from the Internet: < http://en.wikipedia.org/wiki/Alzheimer's_disease >, Accessed on Aug. 14, 2013, 28 pgs.

(Continued)

*Primary Examiner* — Bruk Gebremichael
(74) *Attorney, Agent, or Firm* — Kwan & Olynick LLP

(57) ABSTRACT

Various embodiments of the present invention describe mechanisms configured to monitor, track, and manage symptoms of Alzheimer's disease (AD). According to particular embodiments, a system includes an interface configured to present a memory test to a user and an interface configured to receive a response to the memory test. The system includes a processor that is configured to determine whether the user experienced a memory lapse based on the response to the memory test. The system further includes a computer memory configured to store data related to the memory lapse and memory ratings over time. Memory ratings and Alzheimer's disease progression ratings can be displayed using the system.

20 Claims, 5 Drawing Sheets

(56) References Cited

U.S. PATENT DOCUMENTS

| | | | |
|---|---|---|---|
| 2013/0082837 A1* | 4/2013 | Cosentino | G06F 19/3418 340/539.12 |
| 2013/0316746 A1* | 11/2013 | Miller | H04L 51/30 455/466 |

OTHER PUBLICATIONS

"Alzheimer's Disease Fact Sheet", [Online]. Retrieved from the Internet: < http://www.nia.nih.gov/alzheimers/publication/alzheimers-disease-fact-sheet >, Accessed on Aug. 14, 2013, 6 pgs.

* cited by examiner

MONITORING, TRACKING, AND MANAGING SYMPTOMS OF ALZHEIMER'S DISEASE

TECHNICAL FIELD

The present disclosure relates to monitoring, tracking, and managing symptoms of Alzheimer's disease.

DESCRIPTION OF RELATED ART

Alzheimer's disease (AD) is a form of dementia and is a progressive, degenerative, and incurable brain disease characterized by declining cognitive function and behavioral abilities. Progression of AD is usually characterized by four stages: pre-dementia, early/mild, moderate, and advanced/severe. However, there is some discrepancy about where the lines are drawn between these stages. Generally, pre-dementia or early symptoms include memory problems, absent-mindedness, and misplacing items. Next, the disease progresses such that short-term memory begins to fade, although long-term memory may stay intact. As mild symptoms continue, they may include getting lost, taking longer to complete daily tasks, repeating questions, poor judgment, and mood or personality changes. At this point, family members may be keen to notice changes even before the person exhibiting the symptom notices.

Moderate symptoms may include increasing severity of the previous symptoms, and can further include increasing memory loss and confusion, difficulty recognizing family and friends, difficulty learning new things and coping with new situations, and difficulty carrying out multiple-step tasks. In addition, wandering can increase at this stage. Other symptoms include becoming increasingly aggressive or passive, and experiencing hallucinations, delusions, paranoia, and/or impulsivity. As the disease progresses, symptoms can include initiating the same conversation repeatedly, impaired speech, impaired cognition, more abusive behavior, increased anxiety, and increased paranoia. When AD reaches its most advanced stages, communication and body functions are lost and the sufferer becomes completely dependent on others for care.

There are various theories regarding the causes of AD. However, there are two main theories. One theory includes the formation of amyloid plaques that appear as abnormal clumps in the brain. The other theory includes the formation of neurofibrillary tangles that appear as tangled bundles of fibers formed by abnormal tau proteins. According to both theories, neurons lose their ability to communicate and function over time, causing them to die.

Various techniques can be used to diagnose someone with Alzheimer's disease. One technique uses neuropsychological tests. Another technique includes interviews with family members and caregivers. Both of these techniques include the risk of inaccurate memories, judgments, and observations. Another technique, which is more invasive, involves a spinal tap of cerebrospinal fluid to detect beta-amyloid or tau proteins. Another technique, which is not commercially available, includes neuroimaging techniques. As part of the process of diagnosing Alzheimer's disease, various other conditions or diseases should be ruled out through blood tests. For instance, thyroid function tests should be conducted to exclude the possibility that the symptoms are attributable to thyroid disease. If another cause of the symptoms is found, it is possible that a cure or treatment can be provided. Although various techniques can be used to diagnose Alzheimer's disease, existence of the disease is only certain after death as confirmed by an autopsy.

Alzheimer's disease is incurable, so treatment for the disease is palliative, such that the focus is on easing the pain and symptoms of the disease. Pharmaceutical treatments can be helpful in palliative care, although no drugs can currently halt or delay the onset of the disease. In particular, drugs can be used to help regulate neurotransmitters, which can help with cognitive and behavioral symptoms. In addition, drugs can help with other symptoms such as sleep difficulties, agitation, wandering, anxiety, depression, and anger. Another type of treatment includes psychosocial intervention that can focus on the various symptoms of dementia. The main treatment involves caregiving, the need for which increases as the disease progresses.

Alzheimer's disease is a devastating illness that is progressive and incurable. However, accurate information about progression of the disease is helpful to both doctors and family caring for someone diagnosed with the disease. Specifically, doctors and caregivers can more effectively provide treatments and therapy appropriate for the stage of the illness. Furthermore, family members can plan finances and caregiving more effectively. In addition, information about the progression of the disease can be collected to assist doctors and researchers to better understand the disease and search for a cure. Because current methods of measuring disease progression are often inaccurate, invasive, or commercially unavailable, it is desirable to provide improved mechanisms to gather data about the progression of Alzheimer's disease for a diagnosed individual.

SUMMARY

Various embodiments of the present invention describe mechanisms configured to monitor, track, and manage symptoms of Alzheimer's disease (AD). According to particular embodiments, a system includes an interface configured to present a memory test to a user and an interface configured to receive a response to the memory test. The system includes a processor that is configured to determine whether the user experienced a memory lapse based on the response to the memory test. The system further includes a computer memory configured to store data related to the memory lapse and memory ratings over time. Memory ratings can be displayed using the system.

BRIEF DESCRIPTION OF THE DRAWINGS

The disclosure may best be understood by reference to the following description taken in conjunction with the accompanying drawings, which illustrate particular embodiments of the present invention.

DETAILED DESCRIPTION

Figure 1:
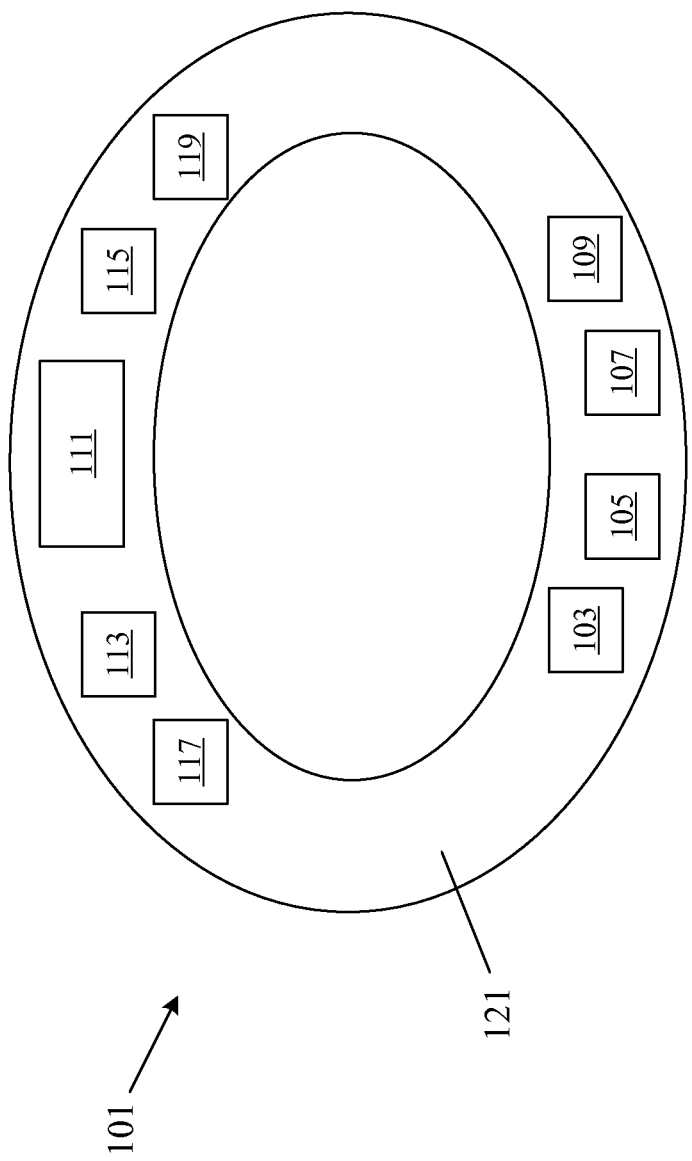
FIG. 1 illustrates one example of a system configured to monitor memory lapses of a user with Alzheimer's disease.

Reference will now be made in detail to some specific examples of the invention including the best modes contemplated by the inventors for carrying out the invention. Examples of these specific embodiments are illustrated in the accompanying drawings. While the invention is described in conjunction with these specific embodiments, it will be understood that it is not intended to limit the invention to the described embodiments. On the contrary, it is intended to cover alternatives, modifications, and equivalents as may be included within the spirit and scope of the invention as defined by the appended claims.

In the following description, numerous specific details are set forth in order to provide a thorough understanding of the present invention. Particular example embodiments of the present invention may be implemented without some or all of these specific details. In other instances, well known process operations have not been described in detail in order not to unnecessarily obscure the present invention.

Alzheimer's disease (AD) is a progressive, degenerative, and incurable brain disease characterized by declining cognitive function and behavioral abilities. AD is a form of dementia and its progression is usually characterized by four stages: pre-dementia, early/mild, moderate, and advanced/severe. Although there is some discrepancy about where the lines are drawn between these stages, pre-dementia or early symptoms can include memory problems, absent-mindedness, and misplacing items. Next, the disease progresses such that short-term memory begins to fade, although long-term memory may stay intact. As mild symptoms continue, they may include getting lost, taking longer to complete daily tasks, repeating questions, poor judgment, and mood or personality changes. At this point, family members may be keen to notice changes even before the person exhibiting the symptom notices.

Moderate symptoms may include increasing severity of the previous symptoms, and can further include increasing memory loss and confusion, difficulty recognizing family and friends, difficulty learning new things and coping with new situations, and difficulty carrying out multiple-step tasks. In addition, wandering can increase at this stage. Other symptoms include becoming increasingly aggressive or passive, and experiencing hallucinations, delusions, paranoia, and/or impulsivity. As the disease progresses, symptoms can include initiating the same conversation repeatedly, impaired speech, impaired cognition, more abusive behavior, increased anxiety, and increased paranoia. When AD reaches its most advanced stages, communication and body functions are lost and the sufferer becomes completely dependent on others for care.

Various techniques can be used to diagnose someone with Alzheimer's disease and determine the stage or progression of the illness. For instance, neuropsychological tests can be given. However, these can be time and labor-intensive to administer. Another technique includes interviews with family members and caregivers. However, using this method involves the risk of inaccurate memories, judgments, and observations. Another technique, which is more invasive, involves a spinal tap of cerebrospinal fluid to detect beta-amyloid or tau proteins. Another technique, which is not commercially available, includes neuroimaging techniques.

Alzheimer's disease is incurable, so treatment for the disease is palliative, such that the focus is on easing the pain and symptoms of the disease. Pharmaceutical treatments can be helpful in palliative care, although no drugs can currently halt or delay the onset of the disease. In particular, drugs can be used to help regulate neurotransmitters, which can help with cognitive and behavioral symptoms. In addition, drugs can help with other symptoms such as sleep difficulties, agitation, wandering, anxiety, depression, and anger.

Another treatment includes psychosocial intervention that can focus on the various symptoms of dementia. The main treatment involves caregiving, the need for which increases as the disease progresses.

Alzheimer's disease is a devastating illness that is progressive and incurable. However, accurate information about progression of the disease is helpful to both doctors and family caring for someone diagnosed with the disease. Specifically, doctors and caregivers can more effectively provide treatments and therapy appropriate for the stage of the illness. Furthermore, by knowing the trajectory of the illness, the family can plan finances and caregiving more effectively. Additionally, information about progression of the disease can be collected to assist doctors and researchers to better understand the disease and search for a cure. However, current methods of measuring the progression of AD are often time-intensive, inaccurate, invasive, or commercially unavailable. Accordingly, it is desirable to provide improved mechanisms to gather data about the progression of Alzheimer's disease for someone living with the disease.

FIG. 1 illustrates one example of a system configured to monitor memory lapses of a user with Alzheimer's disease (AD). As shown, the system 101 includes a band 121 with a memory 103, processor 105, and interface 111. In the present exemplary embodiment, interface 111 is a display or touch screen configured to present a memory test to a user. Some examples of displays that can be used with the present invention include a liquid crystal display (LCD), a flexible organic light emitting diode (OLED) display, a magnetic display, and a microelectromechanical systems (MEMS) display. In some examples, interface 111 can also receive input from a user, such as a response to a memory test presented via interface 111. Alternatively, in some embodiments, system 101 can receive input from the user via buttons 119.

In the present exemplary embodiment, processor 105 is configured to determine whether the user experienced a memory lapse based on the user's response to a memory test. Furthermore, computer memory 103 is configured to store data related to the memory lapse and memory ratings over time. Memory ratings can be displayed through interface 111. According to various embodiments, memory ratings are correlated with Alzheimer's progression ratings.

In some exemplary embodiments, system 101 can include a Global Positioning System (GPS) device 107 or other locating mechanism. This GPS can provide location information of the user, which can be especially helpful in cases when the user is lost or wanders off. This GPS can also provide location information for the system 101 in the event that the system is lost or misplaced.

In some exemplary embodiments, the system can include a network interface 109, which can include a plug, USB connection, Bluetooth, or the like. This network interface can allow the system to communicate and/or exchange data with other devices such as a smart phone, computer, etc. However, it should be noted that the system can be constructed to operate independently without a network interface in some embodiments.

According to various exemplary embodiments, band 121 can optionally include a speaker 113. Speaker 113 can present audio portions of a memory test or narration of text displayed on interface 111. For instance, a song, recording, voice message, or other audio track can be played for the user as part of a memory test, depending on what type of memory test is selected.

Band 101 can also optionally include a notification light 115. In some exemplary embodiments, this notification light can turn on, flash and/or blink when presenting a memory test to a user or requesting a response or other input. Alternatively, this notification light can be used to display system conditions such as battery life, etc. This notification light may be a single color or multiple colors. In particular, the light could display a different color for different types of notifications, such as battery status, sleep mode, awake mode, etc. In other embodiments, the light could take the form of different shapes displayed for different types of notifications. For instance, awake mode could display a light in the shape of an open eye, sleep mode could display a light in the shape of a closed eye, and battery life can display a light in the shape of a battery, etc. The color of the shaped light might indicate whether the battery is fully charged (e.g. green), partially charged (e.g. yellow), or needs charge (e.g. red).

According to various exemplary embodiments, band 121 can optionally include a vibration mechanism 117. The vibration mechanism 117 can be used in various ways. For instance, vibrations can be used when presenting a memory test to a user or requesting a response or other input. In another example, vibrations can be used in conjunction with an alarm or reminder. For instance, the user could set an alarm to check in with a caregiver periodically and band 121 would vibrate according to this schedule.

In some exemplary embodiments, band 121 can include one or more buttons 119. These buttons can be used to control the interface 111, speaker 113, notification light 115, vibration mechanism 117, or other parts of the system 101. For instance, it can be used to make a selection presented by the interface 111, adjust the volume of the speaker 113, and/or activate the notification light 115.

According to the present embodiment, band 121 can be designed as a bracelet, wristband, or other wearable device. Band 121 can be constructed from various materials, such as elastic, plastic, vinyl, rubber, etc. The material of the band can be rigid (like a hard plastic, etc.) or flexible (like silicone, rubber, etc.). According to various embodiments, band 121 can be adjustable in size. For instance, band 101 can include a buckle, latch, or the like. In other examples, band 121 can overlap itself like a slap bracelet, so that it can be sized the user more easily. In another example, band 121 can form a U-shape that can either leave an opening on one portion of the length or overlap itself to some extent. In yet other examples, band 121 can have a clasp that can adjustably attach to links, loops, or other openings on the band 121.

It should be noted that although the present embodiment shows a certain configuration of the components in band 121, the configuration is illustrative only and does not intend to limit the placement of various components. For instance, the location of speaker 113 and buttons 119 can be exchanged. Similarly, other components of the system 101 can be moved with respect to one another without departing from the scope of the present invention.

Figure 2:
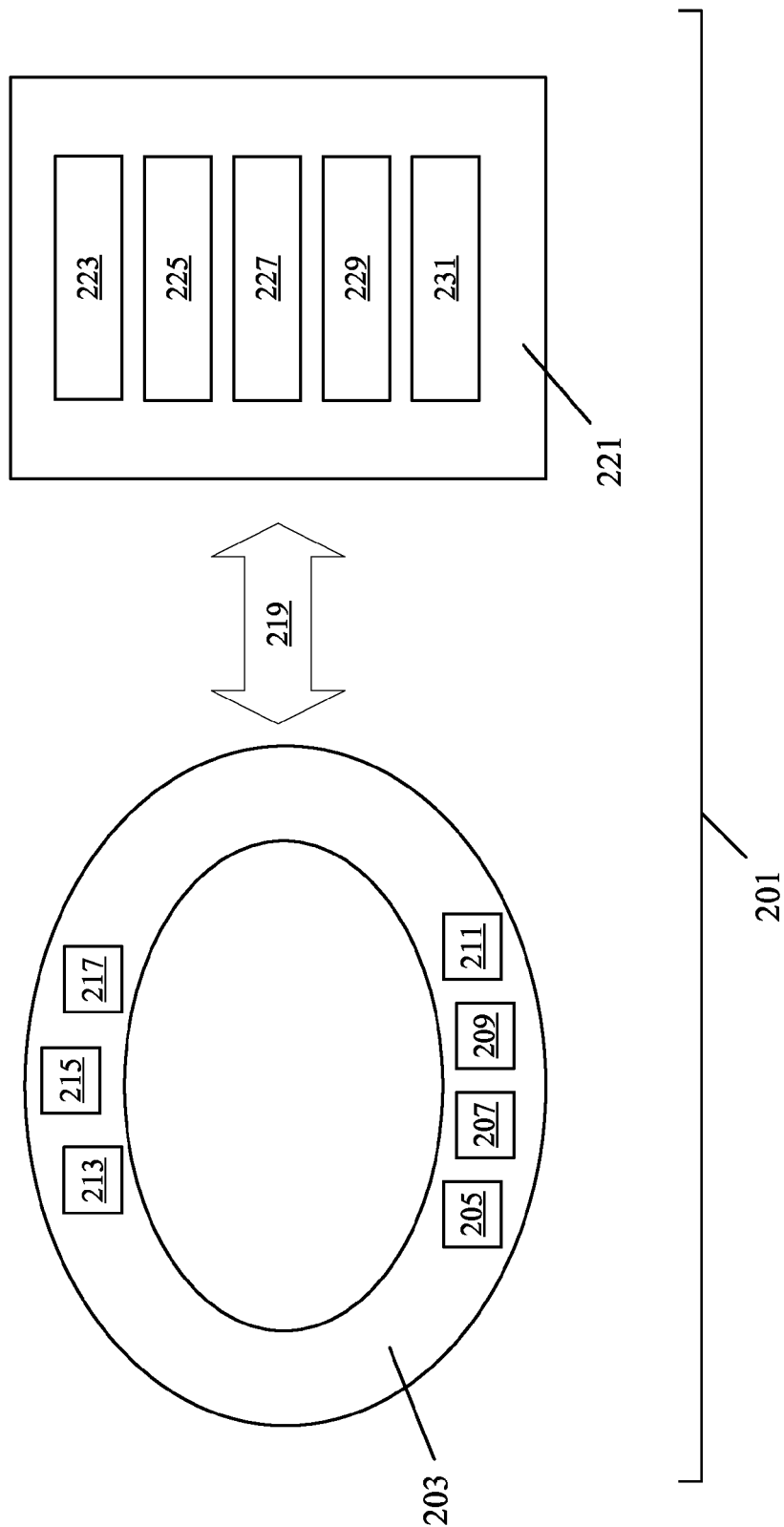
FIG. 2 illustrates another example of a system configured to monitor memory lapses of a user with Alzheimer's disease.

FIG. 2 illustrates another example of a system configured to monitor memory lapses of a user with Alzheimer's disease. As shown, the system 201 includes a band 203 and device 221. According to the present embodiment, band 203 can be designed as a bracelet, wristband, or other wearable device. Furthermore, device 221 can be a smart phone, computer, laptop, tablet, notebook, portable gaming device, or other interactive device.

In the present exemplary embodiment, band 203 can include a notification light 213. This notification light 213 can turn on, flash and/or blink when the user is presented with a memory test or when the user is prompted for a response or other input. Alternatively, this notification light can be used to display system conditions such as battery life, etc. This notification light 213 may display a single color or multiple colors. In particular, the light could display a different color for different types of notifications, such as battery status, sleep mode, awake mode, etc. In other embodiments, the light could take the form of different shapes displayed for different types of notifications. For instance, awake mode could display a light in the shape of an open eye, sleep mode could display a light in the shape of a closed eye, and battery life can display a light in the shape of a battery, etc. The color of the shaped light might indicate whether the battery is fully charged (e.g. green), partially charged (e.g. yellow), or needs charge (e.g. red).

According to various exemplary embodiments, band 203 can optionally include a vibration mechanism 215. The vibration mechanism 215 can be used in various ways. For instance, vibrations can be used when presenting a memory test to a user or requesting a response or other input. In another example, vibrations can be used in conjunction with an alarm or reminder. For instance, the user could set an alarm to check in with a caregiver periodically and band 203 would vibrate according to this schedule.

In the present exemplary embodiment, band 203 can include one or more buttons 217. These buttons can be used to control notification light 213, interact with device 221, or communicate with other parts of the band 203. For instance, it can be used to activate the notification light 213, such as to determine the current mode (e.g. awake, asleep, etc.) or to activate or switch to a certain mode (e.g. change from awake to asleep).

In some exemplary embodiments, band 203 can include a Global Positioning System (GPS) device 205 or other locating mechanism. This GPS can provide location information of the user, which can be especially helpful in cases when the user is lost or wanders off. This GPS can also provide location information for bracelet 203 in the event that the system is lost or misplaced.

According to various exemplary embodiments, band 203 can be constructed from various materials, such as elastic, plastic, vinyl, rubber, etc. The material of the band can be rigid (like a hard plastic, etc.) or flexible (like silicone, rubber, etc.). According to various embodiments, the band 203 can be adjustable in size. For instance, band 203 can include a buckle, latch, or the like. In other examples, band 203 can overlap itself like a slap bracelet, so that it can be sized the user more easily. In another example, the band 203 can form a U-shape that can either leave an opening on one portion of the length or overlap itself to some extent. In yet other examples, band 203 can have a clasp that can adjustably attach to links, loops, or other openings on the band 203.

According to various exemplary embodiments, band 203 can optionally include simple memory 207 and/or simple processor 209. In some examples, simple memory 207 and/or simple processor 209 can be used to detect input from buttons 217. Additionally, simple memory 207 and/or simple processor 209 can be used to control notification light 213.

According to the present embodiment, band 203 includes a network interface 211, which can include a plug, USB connection, Bluetooth, or the like. This network interface 211 can allow the band 203 to communicate and/or exchange data with device 221 such as a smart phone, computer, etc. Such communication can occur over a data connection 219 that can be wired, wireless, etc. depending on the chosen communication protocol.

In the present exemplary embodiment, device 221 includes an interface 223, processor 225, computer memory 227, and speaker 229. Device 215 can be a smart phone, computer, laptop, tablet, notebook, portable gaming device, or other interactive device. In addition, device 221 can exchange, receive, and/or send communications and/or data with band 203 over data connection 219 using network interface 231.

In the present exemplary embodiment, interface 223 can be a display or touch screen configured to present a memory test to a user. Some examples of displays that can be used with the present invention include a liquid crystal display (LCD), a flexible organic light emitting diode (OLED) display, a magnetic display, and a microelectromechanical systems (MEMS) display. In some examples, interface 223 can also receive input from a user, such as a response to a memory test presented via interface 223. Alternatively, in some embodiments, system 201 can receive input from the user via buttons 217 or buttons located on device 221.

In the present exemplary embodiment, processor 225 is configured to determine whether the user experienced a memory lapse based on the user's response to a memory test. Furthermore, computer memory 227 is configured to store data related to the memory lapse and memory ratings over time. Memory ratings can be displayed through interface 223.

In the present embodiment, device 221 includes speaker 229. Speaker 229 can present audio portions of a memory test or narration of text displayed on interface 223. For instance, a song, recording, voice message, or other audio track can be played for the user as part of a memory test, depending on what type of memory test is selected.

In the present embodiment, band 203 and device 221 can work together to provide memory tests to the user. For instance, band 203 can blink and vibrate when it is time to start a memory test. The user would then access device 221 for a presentation of the memory test. The user can then provide a response or input via device 221 or using buttons 217 on band 203. Data regarding the memory tests can be accessed and displayed on device 221. In this embodiment, band 203 would be able to provide reminders and notifications to the user without the user having to carry around or be constantly near device 221.

It should be noted that although the present embodiment shows a certain configuration of the components in band 203 and remote device 221 of system 201, the configuration is illustrative only and does not intend to limit the placement of various components. For instance, the location of notification light 213 and vibration mechanism 215 can be exchanged within band 203. Furthermore, the placement of interface 223 can be exchanged with speaker 229 within remote device 221. Similarly, other components of the system 201 can be moved with respect to one another without departing from the scope of the present invention.

In an alternative embodiment, system 201 can include only device 221, without band 203. In this alternative embodiment, the user would be presented with memory tests and would provide memory tests through device 221. In some examples, device 221 would also include a GPS, to allow location of the device and/or user. This alternative embodiment provides a simpler system in that there is only one component for the user to maintain. However, the user must keep the device nearby constantly to be able to hear or feel notifications from the device and be reminded of a memory test.

Figure 3:
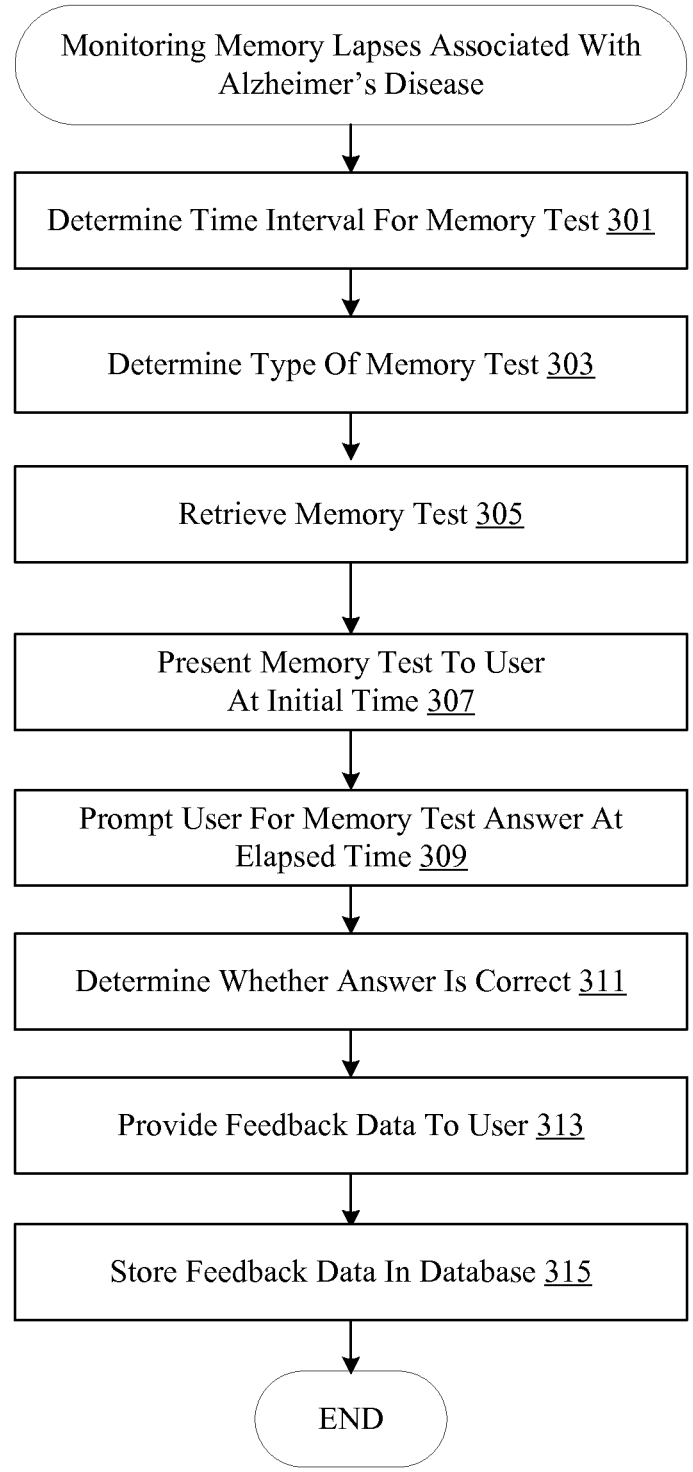
FIG. 3 illustrates an example of monitoring memory lapses of a user with Alzheimer's disease.

FIG. 3 illustrates an example of monitoring memory lapses of a user with Alzheimer's disease. Specifically, the user engages with a system such as one shown in FIGS. 1 and 2. The system can then monitor the user's memory by presenting one or more memory tests the user.

According to the present exemplary embodiment, the system first determines the time interval over which the memory test will span at 301. For instance, a span of 3 hours could be chosen for a short-term memory test in which a response is provided initially, and a prompt for this response is given at 3 hours. In contrast, a short span of a few minutes may be long enough to present a question and receive a response for a long-term memory test.

Next, the system determines the type of memory test to be presented at 303. For instance, a short-term memory test might provide a response such as the color red. The user will then be told that this response should be provided when prompted later by the system. When the prompt is given a few hours later, the user is then asked to tell the system what color they were previously given. Similarly, other short-term memory tests can provide responses such as colors, numbers, letters, words, songs, images, audio, video, phrases, etc. that the system will prompt the user about after some elapsed time. For instance, the system can instruct the user to tap a button three times or enter the number three when asked at a later time. In some examples, the user can select from multiple choice responses. In contrast, a long-term memory test might provide a question or prompt to see if the user remembers something that is a part of the user's life. For instance, the user can be asked a question such as what year they graduated from high school or the name of their high school. The response can be already stored in a database of information about the user. Other examples include displaying a picture of a friend or loved one to the user and asking the user to identify the person in the picture, providing an audio clip and asking the user to identify the voice of someone familiar, or providing a video clip and asking the user to identify the video. In some examples, the user can choose from multiple choice responses.

In the present embodiment, the system then retrieves a memory test at 305 based on the time interval and the type of memory test that was chosen. Next, at 307, the memory test is presented to the user at an initial time. For instance, if a short-term memory test was chosen, a response or instructions about what the user should input when prompted at a later time is provided. In some embodiments, the user can be explicitly informed about what time the prompt will be given. In other embodiments, the user might just be informed that a prompt will be given later. However, if a long-term memory test was chosen, a question that could be answered according to the user's long-term memory is provided at this initial time.

At 309, the user is prompted for a response to the memory test at an elapsed time. For instance, if the user was presented with a short-term memory test, the elapsed time may have been 3 hours and the user asked to input the number that the system provided at the initial time. In another example, if the user was presented with a long-term memory test, the elapsed time may be very short because the user is presented with a long-term memory question at the initial time and then immediately prompted to answer the question. In some embodiments, the user can be provided with multiple choices for responses. For instance, a user can be provided with four responses and can tap one answer via a touch screen. In other embodiments, buttons or voice recognition could be used.

Next, the system determines whether the user's response or input is correct at 311. In the present embodiment, the system can compare the user's response to the response stored in a database to determine whether the response is correct. If the response is incorrect, a memory lapse can be found to have occurred. Feedback data about whether a memory lapse has occurred can then be provided at 313. For instance, the user can be presented with a display that the response was correct or not correct. Next, the feedback data can be stored in a database at 315.

Figure 4:
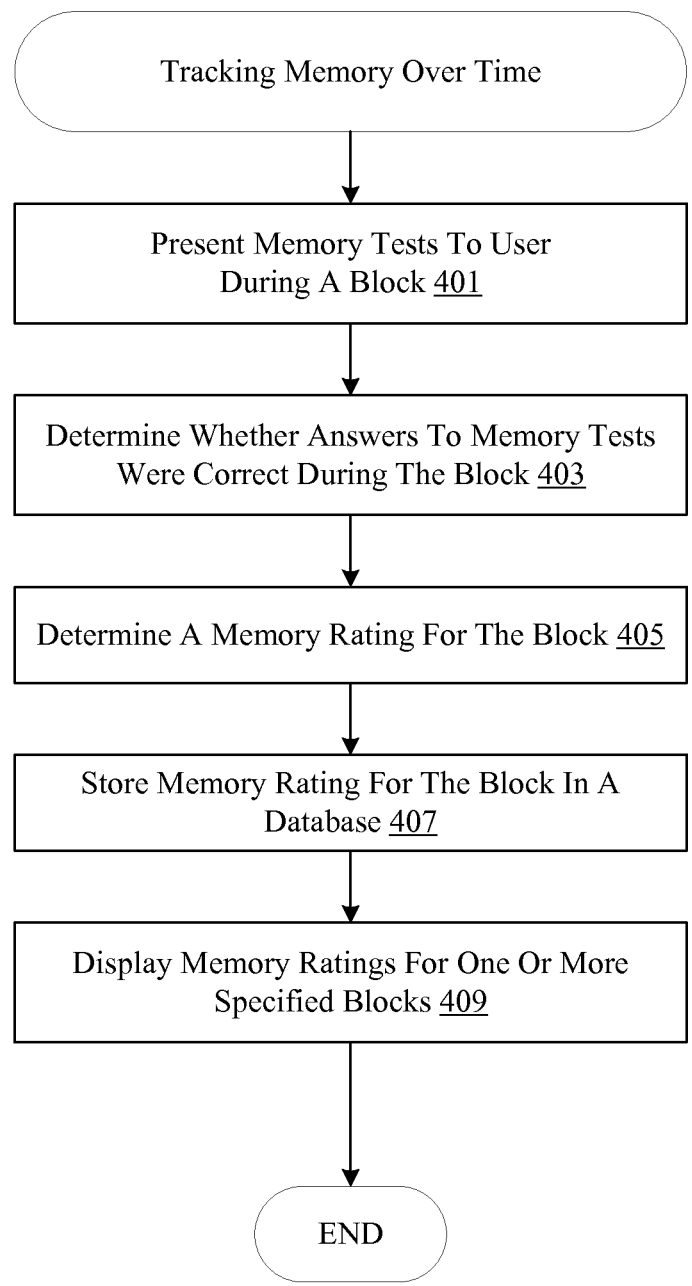
FIG. 4 illustrates an example of tracking the memory of a user with Alzheimer's disease over time.

FIG. 4 illustrates an example of tracking the memory of a user with Alzheimer's disease over time. In the present exemplary embodiment, a user is presented with memory tests spanning a specified block of time at 401. For instance, a user can be presented with two short-term memory tests in one day, where one day is the specified block of time. Next, a determination is made about whether the responses to the memory tests presented in the specified block of time were correct at 403. Specifically, each wrong response could be labeled as a memory lapse. Based on the number of memory lapses, a memory rating is determined for the specified block of time at 405. For instance, a rating of 1 could indicate that all of the responses provided were incorrect and a rating of 10 could indicate that all of the responses provided were correct. So if two memory tests were provided in the specified block of time and both responses were correct, the rating for the specified block of time would be 10. However, if both responses were wrong, the rating for the specified block of time would be 1. Furthermore, if one response was right and one response was wrong, the rating for the specified block of time would be 5. Once the memory rating is determined for the specified block of time, it is stored in a database at 407.

In the present exemplary embodiment, memory ratings can be displayed for specified blocks of time at 409. Specifically, displaying memory ratings for a number of sequential specified blocks of time can show whether the user's memory is declining over time. The memory ratings can be displayed in various formats. For instance, the memory ratings can be displayed as numerical values, in a chart, as a line graph, as a bar graph, etc. In some embodiments, memory ratings can be separated based on long-term and short-term memory tests. However, in some embodiments, both short-term memory ratings and long-term memory ratings can be displayed together to determine if there is any correlation between the two. For instance, a line graph can include two lines versus time, with one line representing short-term memory and one line representing long-term memory. In one example, if memory ratings for short-term memory are declining over time, while staying constant for long-term memory over time, a determination could be made that the disease has not yet progressed to an advanced stage. In another example, if memory ratings for short-term memory are rapidly declining over time and long-term memory are also rapidly declining over time, then a determination could be made that the disease is progressing rapidly. In yet another example, if memory ratings for short-term memory and long-term memory are steady, a determination could be made that the disease is not progressing much.

According to various embodiments, specified blocks of time can be adjusted according to the needs of the user. For instance, the specified blocks of time can be set to one week, so that a doctor can efficiently monitor progress of the disease over a span of a few months. By adjusting the specified blocks of time, new memory ratings can be provided for these adjusted specified blocks of time and the data displayed can be adjusted according to the desires of the user.

Figure 5:
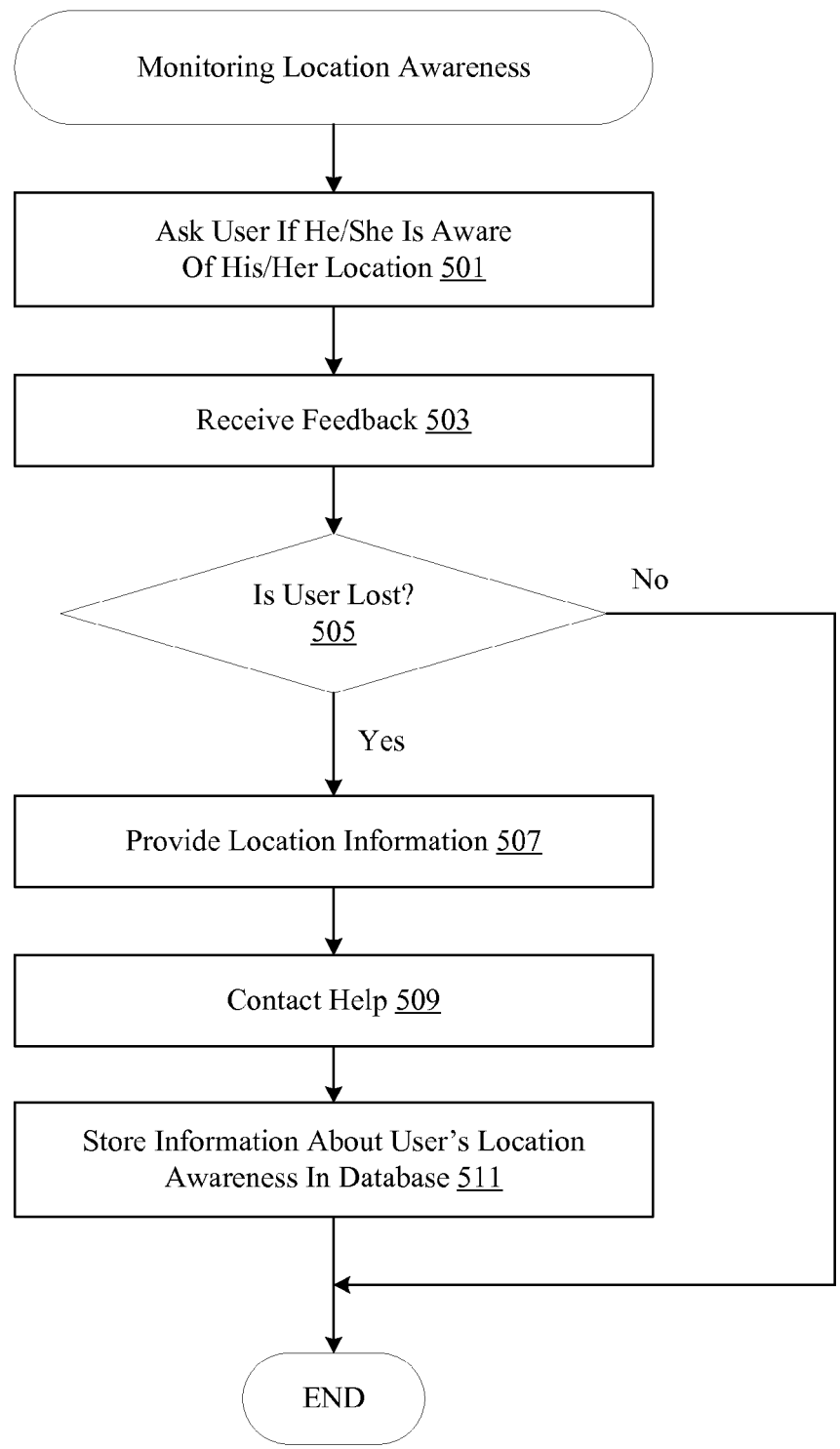
FIG. 5 illustrates an example of monitoring the location awareness of a user with Alzheimer's disease.

FIG. 5 illustrates an example of monitoring the location awareness of a user with Alzheimer's disease. As described above, some people with AD tend to wander or get lost as the disease progresses. In order to provide family, caregivers and doctors information about the user's whereabouts for safety purposes and to provide data about progression of the disease, the present invention provides mechanisms to monitor and manage a user's location awareness.

In the present exemplary embodiment, the user is asked if he/she is aware of his/her location at 501. For instance, the user can be prompted with the question "Where are you?" In this example, the user can be given three choices: "I don't know," "Home," or "Specify a location." The user ca response the question by providing input via a touch screen, buttons, voice recognition, or other input device.

In the present embodiment, feedback is received from the user at 503. Next, a determination is made about whether the user is lost at 505. For instance, if the user selects "I don't know" in response to the choices presented, a determination can be made that the user is lost. If the user selects "Home" or "Specify a location" a determination can be made that the user is not lost. However, in some embodiments, a selection of "Home" or "Specify a location" could lead to one or more follow up questions to verify the selection. For instance, if "Home" is selected, the user may be asked to provide the address of the home. Similarly, if "Specify a location" is selected, the user may be asked to enter a current location. In some embodiments, the location specified by the user can be verified by a GPS locator or other locating device.

According to the present embodiment, if a determination is made that the user is not lost at 505, no further action is taken. However, if a determination is made that the user is lost, then location information can be provided to the user at 507. This location information may include information about the user's whereabouts and how to get home. In some examples, the user can be given instructions such as "Stay there. Help will come soon." In other examples, specific instructions can be given based on information stored in a database. Next, help can be contacted at 509. According to various embodiments, the system can include a transceiver that can be used to contact help. For instance, a friend, family member, or caregiver can be contacted from a list of contacts and provided with location information for the user and that the user is lost. In some embodiments, the user can be put in contact directly with the contact via phone, text, or other communication mechanism.

In the present exemplary embodiment, information about the user's location awareness can be stored in a database at 511. This information can be used by doctors, family, and caregivers to determine whether getting lost is an increasing problem for the user and whether more direct caregiving is desirable or whether limiting the user's mobility might be a good option, such taking away the user's car if the user often gets lost when driving. This information can also be used to assess the progression of the disease.

While the invention has been particularly shown and described with reference to specific embodiments thereof, it will be understood by those skilled in the art that changes in the form and details of the disclosed embodiments may be made without departing from the spirit or scope of the invention. It is therefore intended that the invention be interpreted to include all variations and equivalents that fall within the true spirit and scope of the present invention.

What is claimed is:

1. A system for monitoring the progression of Alzheimer's disease, the system comprising:
   an electronic device comprising:

a first output interface configured to present a memory test to a user at repeated periodic intervals;

an input interface configured to receive a response to the memory test from the user;

a processor connected to the output interface and input interface, the processor configured to determine whether the user experienced a memory lapse and generate a memory rating; and computer memory configured to store data related to the memory lapse and variations in the memory rating over time; and a bracelet worn by the user, the bracelet including:
a processor;
memory;
a multi-colored light, the multi-colored light configured to display different colors for different types of notifications;
a notification mechanism for displaying:
notifications for presenting memory tests at the first output interface of the electronic device, wherein the bracelet works in conjunction with the electronic device to present the memory tests to the user,
notifications for prompts for user input, and
notifications for system conditions;
a network interface to communicate with the electronic device;
buttons for inputting user input; and
a GPS device;

wherein the system is configured to determine whether the user is lost and then provide the user with location information upon determining that the user is lost, wherein determining that the user is lost is determined by displaying a question to the user, said question comprises a plurality of answer choices for selection by the user, including a first choice, a second choice and a third choice; and wherein selecting the second choice or the third choice causes one or more follow-up questions for subsequent display to the user;

wherein variations in the memory rating over time are used to identify an Alzheimer's disease progression rating corresponding to the user.

2. The system of claim 1, further comprising a transceiver configured to contact help when the user does not respond appropriately to repeated memory tests.

3. The system of claim 1, wherein the bracelet also includes an interface for presenting the memory test to the user.

4. The system of claim 1, wherein the memory test comprises a short-term memory test presented to the user on a daily basis.

5. The system of claim 4, wherein the memory test comprises a long-term memory test presented to the user on a weekly basis.

6. The system of claim 1, wherein the memory test includes providing a picture of a person familiar to the user.

7. The system of claim 1, wherein the bracelet includes a vibration mechanism.

8. The system of claim 1, wherein the bracelet also includes speakers.

9. The system of claim 1, wherein determining whether the user is lost includes prompting the user regarding whether the user knows where the user is currently located.

10. The system of claim 1, wherein the system contacts help using a transceiver if the user is determined to be lost.

11. The system of claim 10, wherein the electronic device is a mobile device.

12. A method for monitoring the progression of Alzheimer's disease, the method comprising:

displaying notifications on a bracelet for presenting a memory test, wherein said bracelet comprises a GPS for determining location;

presenting, at a first output interface of an electronic device, a memory test to a user at repeated periodic intervals, wherein the bracelet works in conjunction with the electronic device to present the memory test to the user;

displaying notifications on the bracelet for prompting the user for user input, the notifications being displayed via a multi-colored light, the multi-colored light configured to display different colors for different types of notifications;

transmitting the user input from the bracelet to the electronic device via a network interface on the bracelet;

receiving, at an input interface of the electronic device, a response to the memory test at an input interface configured to receive the response from the user;

determining, via a processor of the electronic device, whether the user experienced a memory lapse by determining whether the user is lost and then providing the user with location information upon determining that the user is lost, wherein determining that the user is lost is determined by displaying a question to the user, said question comprises a plurality of answer choices for selection by the user, including a first choice, a second choice and a third choice; and wherein selecting the second choice or the third choice causes one or more follow-up questions for subsequent display to the user; and storing data related to the memory laps and variations in the memory rating over time in computer memory;

wherein variations in the memory rating over time are used to identify an Alzheimer's disease progression rating corresponding to the user.

13. The method of claim 12, wherein a transceiver coupled to the electronic device is configured to contact help when the user does not respond appropriately to repeated memory tests.

14. The method of claim 12, wherein the memory test comprises a short-term memory test presented to the user on a daily basis.

15. The method of claim 14, wherein the memory test comprises a long-term memory test presented to the user on a weekly basis.

16. The method of claim 12, wherein the memory test includes providing a picture of a person familiar to the user.

17. The method of claim 12, wherein the bracelet includes a vibration mechanism.

18. The method of claim 12, wherein the bracelet also includes speakers.

19. The method of claim 12, wherein the bracelet also includes an interface for presenting the memory test to the user.

20. The method of claim 12, wherein the bracelet also includes a buttons.

* * * * *